United States Patent
Calleri (10) Patent No.: US 10,167,676 B2
(45) Date of Patent: Jan. 1, 2019

(54) METHOD AND RELATIVE SYSTEM FOR THE IDENTIFICATION OF MALFUNCTIONINGS OF THE DRILL BIT DURING THE DRILLING OF HYDROCARBON WELLS

(71) Applicant: GEOLOG S.R.L., San Giuliano Milanese, Milan (IT)

(72) Inventor: Antonio Calleri, Milan (IT)

(73) Assignee: GEOLOG S.R.L., San Giuliano Milanese (Milan) (IT)

( * ) Notice: Subject to any disclaimer, the term of this patent is extended or adjusted under 35 U.S.C. 154(b) by 72 days.

(21) Appl. No.: 15/446,100

(22) Filed: Mar. 1, 2017

(65) Prior Publication Data
US 2017/0254155 A1 Sep. 7, 2017

(30) Foreign Application Priority Data
Mar. 2, 2016 (IT) .................. 102016000021623

(51) Int. Cl.
| | |
|---|---|
| *G01N 33/00* | (2006.01) |
| *E21B 12/02* | (2006.01) |
| *E21B 47/04* | (2012.01) |
| *E21B 45/00* | (2006.01) |
| *E21B 21/06* | (2006.01) |
| *E21B 49/00* | (2006.01) |
| *E21B 41/00* | (2006.01) |

(52) U.S. Cl.
CPC ............ *E21B 12/02* (2013.01); *E21B 21/067* (2013.01); *E21B 41/0092* (2013.01); *E21B 45/00* (2013.01); *E21B 47/04* (2013.01); *E21B 49/005* (2013.01); *G01N 33/0036* (2013.01)

(58) Field of Classification Search
CPC ........ E21B 12/02; E21B 49/005; G01N 33/00
USPC .......................................... 175/89
See application file for complete search history.

(56) References Cited

U.S. PATENT DOCUMENTS

| | | | |
|---|---|---|---|
| 5,237,539 A | 8/1993 | Selman | |
| 8,556,001 B2 * | 10/2013 | Calleri | E21B 21/067 175/207 |

(Continued)

FOREIGN PATENT DOCUMENTS

CA 2 223 662 A1 6/1999

OTHER PUBLICATIONS

Italian Search Report, dated Nov. 1, 2016, from corresponding Italian application.

*Primary Examiner* — Taras P Bemko
(74) *Attorney, Agent, or Firm* — Young & Thompson (57) ABSTRACT

Disclosed is a method for identification of malfunctioning of a drill bit during drilling of hydrocarbon wells. The method includes measuring the penetration rate of the drill bit, measuring the drilling length, measuring the drilling mud concentration of at least one alkene gas species, measuring the torque at the drill bit, then analyzing the microscopic structure of the drilling cuttings on the basis of the values assumed by these measurements and on the basis of the observations of this microscopic structure. Finally the method generates an alert signal and returns the drill bit to the surface. The method facilitates a system for the early identification of drill bit malfunction due to wear, both in the case of fatigue and in the case of wrong initial choice of the type of drill bit with respect to the lithology of the rocks to be drilled.

20 Claims, 2 Drawing Sheets

(56) References Cited

U.S. PATENT DOCUMENTS

| | | | |
|---|---|---|---|
| 2004/0265176 A1* | 12/2004 | Kerherve | B01D 19/0005 |
| | | | 422/68.1 |
| 2008/0250853 A1* | 10/2008 | Calleri | E21B 21/01 |
| | | | 73/152.19 |
| 2013/0008717 A1 | 1/2013 | Deen | |
| 2014/0150527 A1* | 6/2014 | Calleri | G01N 30/68 |
| | | | 73/23.4 |

* cited by examiner

METHOD AND RELATIVE SYSTEM FOR THE IDENTIFICATION OF MALFUNCTIONINGS OF THE DRILL BIT DURING THE DRILLING OF HYDROCARBON WELLS

BACKGROUND OF THE INVENTION

The present invention relates to a method and relative system for the early identification of malfunctionings of the drill bit due to wear of the same during the drilling of hydrocarbon wells.

The state of the art whereto the present invention relates is that of explorations of the subsoil aimed at exploiting its geothermal and oil resources.

In the procedures of drilling of a well for the extraction of hydrocarbons the choice of the drill bit of the auger is of fundamental importance for the purpose of efficiency of drilling. This choice is carried out, in general, by taking as reference the performances of drill bits used previously in nearby and/or similar contexts and wells (offset wells) or in lithotypes which are expected to be encountered also in the well in question. More particularly, drill bits of different materials and shapes are chosen, according to the features of mechanical resistance to the compression of the lithotypes foreseen.

In the case of "soft rock formations" (e.g. non-consolidated sands, clays, soft limestone, shale, red beds, etc.), drill bits are used whose cutting surface is provided with long teeth or elements with chisel shape distanced once from the other, which allow high rates of advancement with little weight and a high number of revs. In the case where traversing of "medium rock formations" (calcite, dolomite, medium limestone, etc.) is foreseen, drill bits with teeth that are close one in relation to the other will be chosen, with respect to those of drill bits used for soft rocks. Finally, the possibility is foreseen of encountering "hard rock formations" (e.g. hard sands, hard calcite, mudstones, etc.), the drill bits to be chosen will have teeth that are even shorter and closer together compared to the previous cases and work more by abrasion than by compression. While the shorter inserts, on the one hand, have lower rates of advancements caused by a rather high number of revolutions, and little weight on the drill bit, on the other hand they have a greater resistance to fatigue and can remain in the well for a longer time before wearing out.

In order to choose the most suitable type of drill bit and best optimise the drilling parameters, it would be necessary, therefore, to know exactly the lithology of the area is going to be drilled. The information that is available before digging a well, such as, for example, that derived from adjacent and/or similar contexts such as offset wells can, however, give only an approximate idea of the actual situation of the subsoil.

Situations may, therefore, occur in which the initial forecasts are wrong and the drill bit is incorrectly selected with respect to what the real lithology of the well required. This leads to premature wear of the drill bit, which becomes unusable before having reached the required depths. This wear can go as far as to cause the breakage of the drill bit with the detachment of pieces of the drill bit itself. When the drill bit has to be extracted and replaced, the manoeuvre of extraction and descent of the new drill bit may take from many hours up to a few days, in cases where it is also necessary to recover any fragments of non-negligible dimensions, worn, detached from the worn drill bit. The times required to bring the worn drill bit and its possible fragments back up and the times of descent of the new drill bit are, obviously, dead times, which increase in a non-negligible way the cost of drilling.

Similar situations may occur in the event of malfunctioning of the drill bit due, not to a wrong choice of the same with respect to the lithology, but simply to the consumption of the drill bit through fatigue. The average life of a drill bit is, in fact, in any case limited, even when this is used with the rocks most suitable for its morphology. It is obvious that, also in the case of wear due simply to fatigue, it is important to be able to realise as soon as possible that the drill bit is now impaired, to avoid unnecessarily continuing to drill and to prevent that there are breakages with detachment of fragments of the same drill bit, resulting in a waste of working hours.

The only parameter which, currently, can be used as a possible indicator of the fact that the drill bit is not able to drill adequately, or because its morphology is not suited to the rock formations encountered, or because it is worn due to fatigue, is the rate of penetration. The latter is commonly known in the industry with the expression "rate of penetration" (ROP). The first suspicion that there is an error in the choice of the drill bit or that the drill bit is consumed due to fatigue, occurs, in fact, when there is an abrupt drop in said rate of penetration. A sudden decrease in the rate of penetration, however, may not necessarily be caused by a malfunctioning of the drill bit, but also by any anisotropies of the lithology of the subsoil during drilling. It is possible, in fact, that a temporary drop in the rate of penetration occurs, without this entailing the drill bit being replaced. Bringing the drill bit back to the surface simply because a decrease in the rate of penetration has been observed may be a mistake if this decrease is due to causes different from wear of the drill bit. Vice versa, it may happen that drilling continues, waiting until the rate of penetration is truly reduced to the minimum. In such cases, that is if the drilling is not interrupted in time, in addition to the waste of time and resources due to the fact that drilling continues with low efficiency, the fracture of the drill bit parts may even take place. As already mentioned above, these parts remain at the bottom of the well and should, therefore, be recovered, with a further waste of hours of work. In light of these considerations it can clearly be seen that the single rate of penetration is not enough to be able to take any decisions on interruption of drilling and on the recovery of the drill bit at the surface.

At the state of art, some methods are known, that in order to overcome this limitation, merge the information about the rate of penetration of the auger with other information, such as, the hydrogen concentration in the drilling mud. The patent application CA2223662A1 describes, indeed, a method for the identification of malfunctioning of the drill bit, which, includes the measurement of the drilling depth and of the rate of penetration of the drill bit, the measurement of hydrogen concentration in the drilling mud and the use, as indicator of malfunctioning of the drill bit, of the combination of the increasing of the hydrogen concentration and of the decreasing of the rate of penetration. In the patent application US 2013/008717, are also mentioned the radioisotope concentration and the concentration of nickel, zinc, silver or copper, as indicators of malfunctioning.

SUMMARY OF THE INVENTION

A first object of the present invention is, therefore, to provide a method and relative system for the early identification of drill bit malfunctionings due to wear of the same, both in the case of fatigue and in the case of wrong initial choice of the type of drill bit with respect to the lithology of the rocks to be drilled.

A second object of the present invention is also to provide a method and relative system for confirming the correctness of the selection made of the type of drill bit, with respect to the lithology of the well being drilled.

A third object of the present invention is, finally, to provide a method and relative system that allows information to be obtained which can be useful for the selection of the type of drill bit in future drillings, said drillings occurring in similar contexts.

These objects are achieved by a method which consists in integrating the information coming from the rate of penetration of the drill bit with one or more other physical and chemical parameters, among which there are measurements of concentration of some particular gaseous components, measurements on the mechanical performances of the same drill bit and measurements on the characteristics of the rocky cuttings produced during drilling and brought to the surface by the drilling mud.

A first of these parameters is constituted by the measurement of concentration of certain gas species, commonly known in the field with the expression "contaminant gases" or "contamination gases". Said gases are alkenes, i.e. acyclic hydrocarbons that have molecular formula $C_nH_{2n}$ and contain a double bond C=C. Examples of alkenes are ethylene, propylene, etc. The alkenes are produced as a result of a phenomenon known by the term "cracking" which essentially consists in the breaking of molecules of heavy hydrocarbons, said breakage being able to take place thermally (i.e. in conditions of high temperature and pressure) or catalytically (i.e. in non-high temperature and pressure conditions and in the presence of a catalyst). In the method which is the object of the present invention reference is made, in particular, to the alkenes produced through thermal cracking.

When the drill bit does not function correctly and there are difficulties in the advancement of the same, both in the case of wear due to fatigue and in the case of problems due to a wrong initial choice of the type of drill bit, a temperature increase occurs in the area being drilled. This increase in the temperature can reach values comprised between 500° C. and 1000° C. When the temperature reaches these levels, the phenomenon of thermal cracking occurs, as mentioned above, with consequent production of alkenes.

An increase in the concentration of alkenes in the drilling mud is therefore an indication of an increase in the temperature in the place of drilling and, therefore, of a malfunctioning of the drill bit. As a result of experimental measurements, at wells in which drill bits not suitable for the local lithology had been used or in which wear phenomena had occurred due to fatigue that resulted in the breaking of the drill bit, it has, in fact, been observed that the measurement of the concentration of alkenes in the drilling mud allows, together with the measurement of the rate of penetration of the auger, the establishing of whether a possible decrease in said rate is due or not to wear of the drill bit. In particular, if the decrease in the rate of penetration is accompanied by an increase in the concentration of alkenes, then the decrease in the rate of penetration is, effectively, due to a malfunctioning of the drill bit, said malfunctioning possibly due to an incorrect choice of the type of drill bit with respect to the lithology of the rock formations being drilled, or to the wear due to fatigue of said drill bit. If, on the contrary, the decrease in the rate of penetration is not accompanied by an increase in the concentration of alkenes, then the decrease in the rate of penetration cannot be attributed to a malfunctioning of the drill bit, or at least to such a malfunctioning such as to make its immediate ascent to the surface necessary.

The method that is the object of the present invention provides, therefore, that the rate of penetration of the drill bit, the drilling length and the concentration in the drilling mud of at least one gas species belonging to the group of alkenes are measured, that such measurements are stored on a computer, are displayed on a monitor and that on the basis of the values assumed by these measurements the drill bit is brought to the surface or not.

The method that is the object of the present invention provides, further, that these measurements of the rate of penetration of the drill bit, of drilling length and of concentration in the drilling mud of at least one gas species belonging to the group of alkenes are processed and compared with the threshold values by said computer, and, finally, that on the basis of the results of this comparison an alert signal is generated, indicative of the need to bring the drill bit back to the surface.

The system that allows implementation of the method which constitutes the object of the present invention provides for the presence of means for measuring the rate of penetration of the auger, means for measuring the length of drilling, means for extracting gases dissolved in the drilling mud, means for measuring the concentration of the alkene gases extracted by said extraction means, means for storing and means for the processing of measurements of the rate of penetration, of the drilling length and of the measurements of concentration of the alkenes and means for the generation of the alert signal. It is evident that the means for storing the measurements of the rate of penetration, of the drilling length and of the concentration of the alkene gases, the means for the processing of such measurements, as well as the means for the generation of the alert signal, can be constituted by a single computer that performs all the functions.

The information relating to the rate of penetration of the drill bit can be integrated not only with the information relating to the concentrations of alkenes in the drilling mud but also with another parameter: the torque at the drill bit. As a result of experimental measurements, at wells in which drill bits had been used not suitable for the local lithology or in which wear phenomena had occurred due to fatigue also resulting in the breakage of the drill bit, it has been observed, in fact, that the drill bit malfunctionings are accompanied by a change to the time trend of the torque. In particular, it has been observed that the time series formed by the torque values assumes an erratic trend, i.e. it no longer follows any regular and recognisable pattern, said values varying in a completely randomised manner. This erratic trend can be for example identified by means of appropriate operations of analysis of the signals, aimed at the determination of the non-predictability of the values assumed by said torque. By way of an example mention can be made here of whiteness tests that determine how far a certain time series is comparable or otherwise to white noise. It is recalled here, for greater clarity, that a signal is defined as white noise and, therefore, a time series, in which the value at a given instant is independent of the values assumed in all the other instants. A signal with such characteristics does not follow any time trend with a recognisable and predictable pattern, but has, in fact, an erratic trend.

The method of the present invention can provide, therefore, that, in addition to the measurements of the rate of penetration of the drill bit, of the drilling length and of the concentration in the drilling mud of at least one gas species, belonging to the group of alkenes, the torque at the drill bit is also measured. Similarly to what is described above, these measurements are then stored in a computer and displayed on a monitor. On the basis of the values assumed by measurements of the rate of penetration of the drill bit, of the drilling length and of the concentration of alkenes in the mud and on the basis of the time trend of the torque, said time trend being displayed on a monitor, the drill bit is brought back to the surface or otherwise.

The method of the present invention provides, moreover, that the measurements of the rate of penetration of the drill bit, of the drilling length, of the concentration in the drilling mud of said at least one gas species belonging to the group of alkenes and of the torque at the drill bit are processed by a computer. In particular these processings consist in the comparison of the rate of penetration and of the concentration of the alkenes with threshold values and in the analysis of the time trend of the torque, said analysis being aimed at evaluation of the erratic nature of said time trend. On the basis of the results of these processings, an alert signal is therefore generated, indicative of the need to bring the drill bit back to the surface.

The system that allows implementation of the method described above provides, therefore, as well as the presence of the means mentioned above, also the presence of means for measuring the torque at the drill bit, means for storing the values of the torque and means for processing of these values. In this case too, it is evident that the means for the storage of the measurements of the rate of penetration, of the drilling length, of the concentration of alkene gases and of the torque at the drill bit, the means for the preparation of these measurements, as well as the means for the generation of the alert signal, can be constituted by a single computer that performs all the functions.

The information relating to the rate of penetration of the drill bit, to the concentrations of alkenes in the drilling mud and to the torque at the drill bit can be, further, integrated with information relating to the microstructural characteristics of the cuttings extracted from the drilling mud. In fact, as described above, when the drill bit is not functioning correctly and there are difficulties in the advancement of the same, both in the case of wear due to fatigue and in the case of problems due to a wrong initial choice of the type of drill bit, in the area being drilled a temperature increase occurs up to values comprised between 500° C. and 1000° C. When the temperature reaches these levels, in the surrounding rocks a phenomenon, known in literature by the term "pyrometamorphism" or "contact metamorphism" occurs, which consists of the textural and compositional alteration of the individual lithotypes subjected for a variable period to high temperatures. The term of "pyrometamorphism" is usually used, both to indicate changes that occur on a geological scale, and to indicate transformations that occur as a result of short and intense temperature variations. In particular, it is known in literature that rocks heated to very high temperatures for a very short time range, followed by a rapid dissipation of heat, can be converted into vitreous and pseudo-vitreous materials, or even undergo a process of carbonisation.

The presence of rocks which have undergone pyrometamorphic transformations, said transformations consisting, mainly, in the vitrification and in the carbonisation of the rocks themselves, is, therefore, an indication of a temperature increase in the place of drilling and, therefore, of a malfunctioning of the drill bit.

The method that is the object of the present invention can provide, therefore, that, in addition to the measurements of the rate of penetration of the drill bit, of the drilling length, of the concentration in the drilling mud of at least one gas species, belonging to the group of alkenes, of the torque at the drill bit, drilling cuttings is also analysed in order to verify the successful pyrometamorphic transformation thereof. Said pyrometamorphic transformation can be a partial or complete vitrification or a total carbonisation.

In a wholly similar way to what is described above, the measurements of the rate of penetration, of the drilling length, of the concentration of alkenes, of torque at the drill bit and the results of the analyses of the drilling cuttings are then stored in a computer and displayed on a monitor. On the basis of the values assumed by the measurements mentioned above and on the basis of the geological characteristics of the drill cuttings, said characteristics being related to the successful vitrification or carbonisation of said cuttings, the drill bit is brought back to the surface or not.

The system that allows implementation of the method described above comprises, in addition to the means mentioned above, also means for the taking of rock samples and means for displaying the microscopic structure of these samples.

DETAILED DESCRIPTION OF THE PREFERRED EMBODIMENTS

Figure 1A:
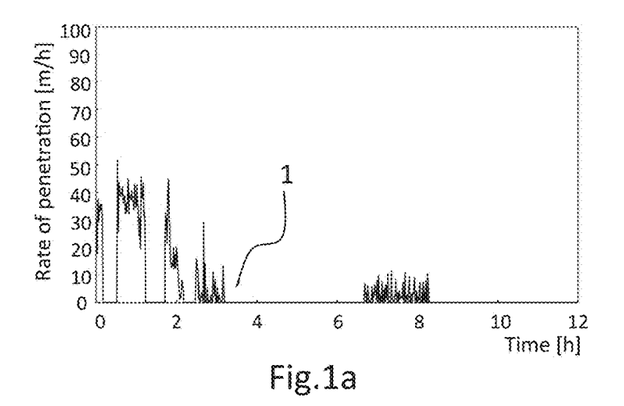
FIG. 1a is a time series of the values of the rate of penetration of a drill bit, measured during an experimental observation carried out in a first drilling well. On the axis of ordinates the rate measured in meters per hour [m/h] is represented, and on the axis of abscissas the time in hours [h] is represented.
Figure 1B:
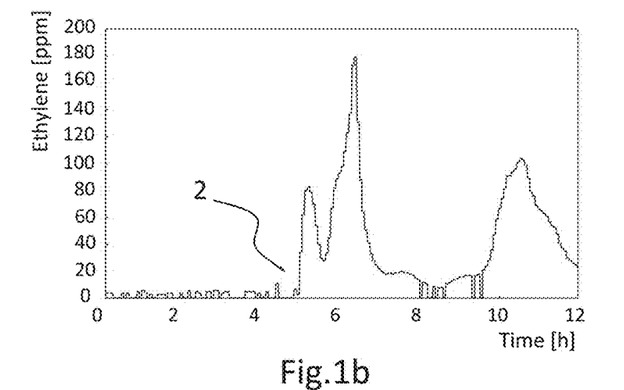
FIG. 1b is a time series of the values of the ethylene concentration in the drilling mud, measured during an experimental observation carried out in a first drilling well. On the axis of ordinates the concentration of the ethylene in the drilling mud measured in parts per million [ppm] is represented, and on the axis of abscissas the time in hours [h] is represented.
Figure 1C:
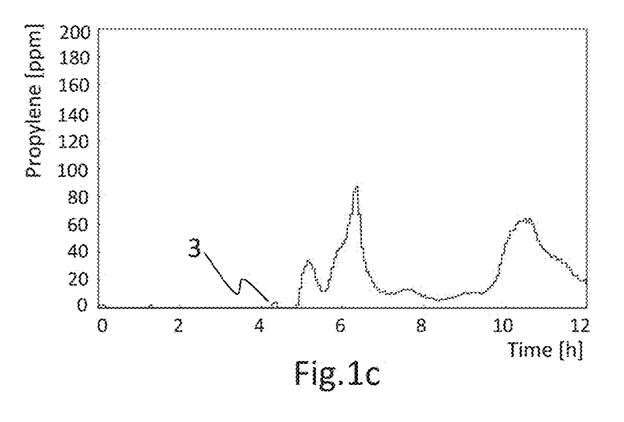
FIG. 1c is a time series of the values of concentration of propylene in the drilling mud, measured during an experimental observation carried out in a first drilling well. On the axis of ordinates the concentration of propylene in the drilling mud measured in parts per million [ppm] is represented, and on the axis of abscissas the time in hours [h] is represented.
Figure 2A:
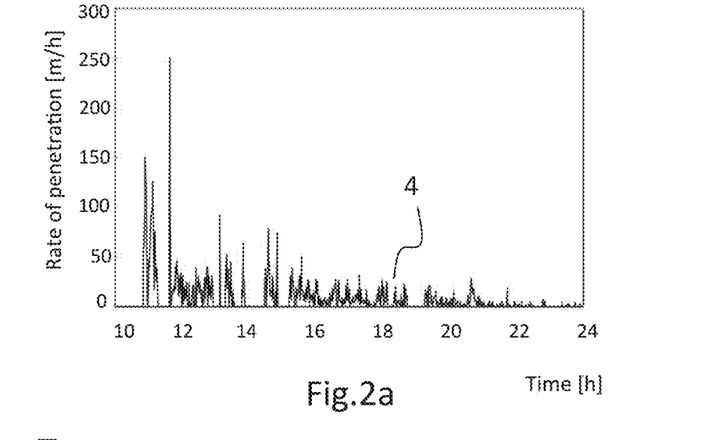
FIG. 2a is a time series of the values of the rate of penetration of a drill bit, measured during an experimental observation carried out in a second drilling well. On the axis of ordinates the rate measured in meters per hour [m/h] is represented, and on the axis of abscissas the time in hours [h] is represented.
Figure 2B:
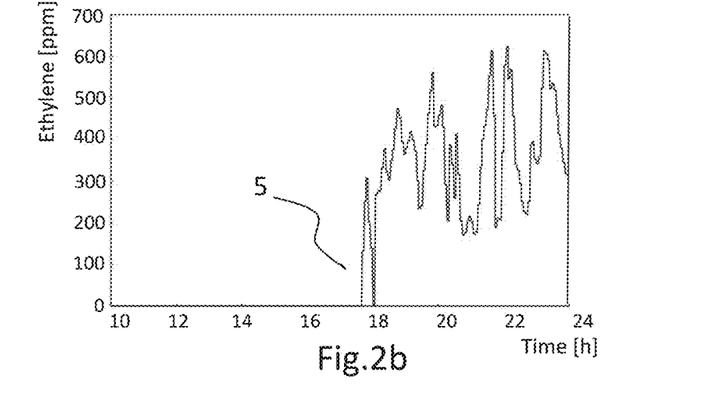
FIG. 2b is a time series of values of the ethylene concentration in the drilling mud, measured during an experimental observation carried out in a second drilling well. On the axis of ordinates the concentration of the ethylene in the drilling mud measured in parts per million [ppm] is represented, and on the axis of abscissas the time in hours [h] is represented.

A first embodiment of the method of the present invention comprises at least the following steps:
  measurement of the drilling depth, obtaining a first time series of the values assumed by said drilling depth, said first time series being stored in a computer;
  measurement of the rate of penetration of the auger during drilling, obtaining a second time series of the values assumed by said rate of penetration, said second time series being stored in a computer. Examples of the time series of the values of rate of penetration are shown in FIGS. 1a and 2a;
  extraction of the drilling mud;
  preferably, heating of said drilling mud;
  degassing of said drilling mud, so as to be able to extract the gases dissolved therein;
  measurement of the concentration in the drilling mud of at least one gas species belonging to the group of the alkenes, obtaining of at least one third time series of the values assumed by said concentration of said at least one gas species, said at least third time series being stored in a computer. Examples of time series of the ethylene concentration are shown in FIGS. 1b and 2b and an example of time series of the concentration of propylene is shown in FIG. 1c;
  for each sample of said second time series, comparison of the value of the rate of penetration corresponding to said sample, with a first threshold value, said step of comparison being carried out by the processor of a computer;
  if the value of said rate of penetration, in correspondence of a certain time sample, hereinafter referred to as "reference", is less than said first threshold value, performing of the following operations:
    calculate the mean value of said rate of penetration, said mean value being measured over a range of time samples, said range of time samples beginning at said reference sample and said range comprising a number of time samples sufficient to cover a range of greater length of drilling or equal to a second threshold value, said operation of calculating the mean value being performed by a processor of a computer;
    comparison of said mean value with said first threshold value, said operation of comparison being performed by a processor of a computer;
    for each sample of said third time series comprised within said range of time samples, said range of time samples beginning at said reference sample and said range comprising a number of time samples sufficient to cover said range of drilling length, comparing of the value of the concentration of said at least one gas species with a third threshold value, said operation of comparing being performed by a processor of a computer;
  if said mean value is less than said first threshold value, and the value of the concentration of said at least one gas species in at least one time sample comprised within said range of time samples is greater than said third threshold value, return the auger to the surface or generate, by means of a processor, an alert signal, said signal being indicative of the need to pull to the surface the drilling battery and replace the drill bit.
Said first threshold value is 2 m/h, said second threshold value is 5 m, and said third threshold value is 25 ppm (parts per million). Said at least one gas species belonging to the group of alkenes can be, for example, ethylene or propylene. The expression "alert signal" refers to any signal provided to the user on the monitor of a computer or by other means of user/computer interface. Referring to FIGS. 1a, 1b and 1c, it is possible to observe how in the well in question, around four hours from the start of data recording, a sharp drop occurred in the rate of penetration (1) of the auger and a corresponding sudden increase in the concentration of ethylene (2) and propylene (3).

A variant of this first embodiment provides that, starting from said first time series, relative to the trend in time of the depth of drilling and from said second time series, relative to the trend in time of the rate of penetration, a fourth series of values is created, said fourth series of values expressing the trend of the rate of penetration as a function of the drilling depth. The values of said fourth series can be obtained by averaging the values of the rate of penetration over a time range, equal to that required to cover a unit of length of the drilling depth. Similarly, starting from said first time series, relative to the trend in time of the drilling depth and from said at least one third time series, relative to the trend in time of the concentration of said at least one gas species belonging to the group of alkenes, at least one fifth series of values can be created, said at least one fifth series of values expressing the trend of the concentration of said at least one gas species as a function of said depth of drilling. The values of said at least one fifth series can be obtained by averaging the values of the concentration of said at least one gas species over a time range, equal to that required to cover a unit of length of the drilling depth.

The system that allows implementation of the first embodiment of the method of the present invention, comprises:
  means for measuring the rate of penetration of the auger;
  means for measuring the drilling length;
  means of extraction from the drilling mud of at least one gas species belonging to the group of the alkenes;
  means for measuring the concentration of said at least one gas species in the drilling mud;
  means for the storage of the measurements of the drilling speed, of drilling length and of concentration of said at least one gas species;
  means for the processing of the measurements of rate of penetration, of the drilling length and of said at least one gas species.
  means for the generation of an alert signal, on the basis of the results of said processing, said alert signal being indicative of the need to bring back to the surface the battery and replace the drill bit.

The means of extraction from the drilling mud of at least one gas species, belonging to the group of alkenes, preferably comprise a filtration probe, a heater of the drilling mud and a degasser.

The means for measuring the concentration of said at least one gas species belonging to the group of the alkenes comprise a flame ionisation detector (FID) specific for the detection of the alkenes.

The means for storing the measurements of the advancement rate, of the drilling length and of the concentration of alkene gases, the means for the processing of these measurements, as well as the means for the generation of the alert signal, can be constituted by a single computer that performs all the functions or by several computers.

A second embodiment of the method of the present invention provides, instead, for the integration of the information related to the rate of penetration and to the concentration of the gas species belonging to the group of alkenes, with the torque, or torque, at the drill bit.

The second embodiment of the method of the present invention therefore comprises at least the following steps:

measurement of the drilling depth, obtaining a first time series of the values assumed by said drilling depth, said first time series being stored in a computer;

measurement of the rate of penetration of the auger during drilling, obtaining a second time series of the values assumed by said rate of penetration, said second time series being stored in a computer. Examples of the time series of the rate of penetration are shown in FIGS. 1a and 2a;

extraction of the drilling mud;

preferably, heating of said drilling mud;

degassing of said drilling mud, so as to be able to extract the gases dissolved therein;

measurement of the concentration in the drilling mud of at least one gas species belonging to the group of the alkenes, obtaining of at least one third time series of the values assumed of said concentration of said at least one gas species, said at least one third time series being stored in a computer. Examples of the time series of the ethylene concentration are shown in FIGS. 1b and 2b;

measurement of the torque at the drill bit, obtaining a fourth time series of the values assumed by said torque, said fourth time series being stored in a computer. An example of the time series of the values assumed by the torque is shown in FIG. 1c, for each sample of said second time series, comparing the value of the rate of penetration corresponding to said sample, with a first threshold value, said step of comparing being performed by a processor of a computer;

if the value of said rate of penetration, at a certain time sample, referred to as "reference", is below said first threshold value, performing of the following operations:

calculate the mean value of said rate of penetration, said mean value being measured over a range of time samples, said range of time samples beginning at said reference sample and said range comprising a number of time samples sufficient to cover a range of length of drilling greater than or equal to a second threshold value, said operation of calculating the mean value being performed by a processor of a computer;

comparison of said mean value with said first threshold value, said operation of comparison being performed by a processor of a computer;

for each sample of said third time series comprised within said range of time samples, said range of time samples beginning at said reference sample and said range comprising a number of time samples sufficient to cover said range of drilling length, comparing of the value of the concentration of said at least one gas species with a third threshold value, said operation of comparing being performed by a processor of a computer;

if:

said mean value is less than said first threshold value, the value of the concentration of said at least one gas species in at least one time sample comprised within said range of time samples is greater than said third threshold value; and if said fourth time series assumes an erratic trend;

bring the auger back to the surface or generate, by means of said processor, an alert signal, said signal being indicative of the need to return the battery to the surface and replace the drill bit.

Figure 2C:
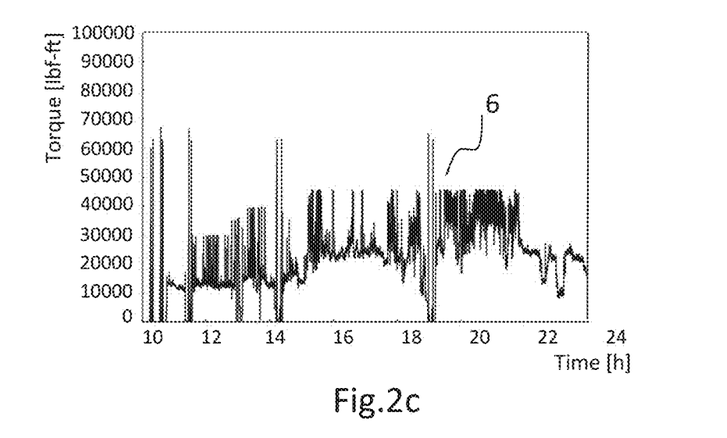
FIG. 2c is a time series of the values of the torque at the drill bit, measured during an experimental observation carried out in a second drilling well. On the axis of ordinates the torque at the drill bit measured in feet by pounds [lb-ft] is represented, and on the axis of abscissas the time in hours [h] is represented.

Said first threshold value is 2 m/h, said second threshold value is 5 m, and said third threshold value is 25 ppm (parts per million). Said at least one gas species belonging to the group of alkenes, can be, for example, ethylene, or propylene. The erratic trend of the time series of the torque values can be identified by any known mathematical method, able to determine this erratic nature, i.e. the non-predictability of the values assumed by the torque. Merely by way of an example, it is possible to mention the so-called whiteness tests that determine to what extent a certain time series is comparable or otherwise to white noise, that is to a time series in which, the value being at a given instant independent of the values assumed in all other instants, it has no recognisable and predictable pattern. Referring to FIGS. 2a, 2b and 2c, it is possible to observe how in the well in question at around eighteen hours after the start of data recording a lowering of the rate of penetration (4) of the auger has occurred, with a corresponding sudden increase in the concentration of ethylene (5) and an evident change (6) in the time trend of the torque at the drill bit, said trend becoming erratic.

Similarly to what is described previously, in relation to the first embodiment, also the second embodiment can provide, in one of its variants which, starting from said first time series, relative to the trend in time of the drilling depth and from said second time series, relative to the trend in time of the rate of penetration, a fifth series of values is created, said fifth series of values expressing the trend of the rate of penetration as a function of the drilling depth. The values of said fifth series can be obtained by averaging the values of the rate of penetration over a time range, equal to that required to cover a unit of length of the drilling depth. Similarly, from said first time series, relative to the trend in time of the drilling depth and from said at least one third time series, relative to the trend in time of the concentration of said at least one gas species belonging to the group of alkenes, at least one sixth series of values can be created, said at least one sixth series of values expressing the trend of the concentration of said at least one gas species as a function of said depth of drilling. A seventh series of values can also be created starting from said first time series relative to the depth of drilling and said fourth time series relative to the trend of the torque, said seventh series expressing the trend of the torque as a function of the drilling depth. The values of said at least one sixth series and of said seventh series can be obtained, respectively, by averaging the values of the concentration of said at least one gas species over a time range, equal to that required to cover a unit of length of the depth of drilling, and by averaging the values of the torque over said time range.

The system that allows implementation of the second embodiment of the present invention, in addition to the means described above, relatively to the first embodiment, comprises:

means for measuring the torque at the drill bit;

means for storing the measurements of torque at the drill bit;

means for the processing of said measurements of torque at the drill bit;

means for the generation of an alert signal, on the basis of the results of processing of the torque measurements and of the measurements of the rate of penetration, of the length of drilling and of the concentration of said at least one gas species of the group of alkenes, said alert signal being indicative of the need to bring back to the surface the battery and replace the drill bit.

Said means for measuring the torque at the drill bit comprise, preferably, hydraulic sensors that measure the pressure variations at the force of rotation of the drill bit rods.

Said means for storing of the measurements of the rate of penetration, of the drilling length, of the concentration of alkene gases and of torque; the means for the processing of these measurements, as well as the means for the generation of the alert signal, can be constituted by a single computer that performs all the functions or by several computers.

A third embodiment of the method of the present invention provides, instead, for the integration of the information related to the rate of penetration, to the concentration of the gas species belonging to the group of alkenes, to the torque at the drill bit with the information relative to the microstructural characteristics of the drilling cuttings.

The third embodiment of the method of the present invention comprises, therefore, at least the following steps:
  measurement of the drilling depth, obtaining a first time series of the values assumed by said drilling depth, said first time series being stored in a computer;
  measurement of the rate of penetration of the auger during drilling, obtaining a second time series of the values assumed by said rate of penetration, said second time series being stored in a computer;
  extraction of the drilling mud;
  taking at intervals corresponding to a drilling length, preferably, greater than or equal to 2 m, a sample of cuttings contained in said drilling mud, said sample weighing, preferably, between 50 and 100 g;
  preferably, heating of said drilling mud;
  degassing of said drilling mud, so as to be able to extract the gases dissolved therein;
  measurement of the concentration in the drilling mud of at least one gas species belonging to the group of the alkenes, obtaining of at least one third time series of the values assumed of said concentration of said at least one gas species, said at least one third time series being stored in a computer;
  analyse, preferably with a high-resolution optical microscope, the sample of previously extracted rock cuttings, in order to display the microscopic structure thereof. Said display is aimed at seeking any vitrifications and carbonisations of the sample;
  measurement of the torque at the drill bit, obtaining a fourth time series of the values assumed by said torque, said fourth time series being stored in a computer;
  for each sample of said second time series, comparing the value of the rate of penetration corresponding to said sample, with a first threshold value, said step of comparing being performed by a processor of a computer;
  if the value of said rate of penetration, at a certain time sample, referred to as "reference", is below said first threshold value, performing of the following operations:
    calculation of the mean value of said rate of penetration, said mean value being measured over a range of time samples, said range of time samples beginning at said reference sample and said range comprising a number of time samples sufficient to cover a range of length of drilling greater than or equal to a second threshold value, said operation of calculating the mean value being performed by a processor of a computer;
    comparison of said mean value with said first threshold value, said operation of comparison being performed by a processor of a computer;
    for each sample of said third time series comprised within said range of time samples, said range of time samples beginning at said reference sample and said range comprising a number of time samples sufficient to cover said range of drilling length, comparing of the value of the concentration of said at least one gas species with a third threshold value, said operation of comparing being performed by a processor of a computer;
  if:
    said mean value is less than said first threshold value,
    the value of the concentration of said at least one gas species in at least one time sample comprised in said range of time samples is greater than said third threshold value;
    said fourth time series assumes an erratic trend; and
    vitrifications or carbonisation were observed under the optical microscope of the sample of drilling cuttings;
  bring the auger back to the surface.

Said first threshold value is 2 m/h, said second threshold value is 5 m, and said third threshold value is 25 ppm (parts per million). Said at least one gas species belonging to the group of alkenes, can be, for example, ethylene, or propylene. The erratic trend of the time series of the torque values can be identified by any known mathematical method, able to determine this erratic nature, i.e. the non-predictability of the values assumed by the torque.

In a manner entirely similar to that described previously, relatively to the second embodiment, the third embodiment can also provide, in one of its variants, that a fifth series of values is created, which expresses the trend of the rate of penetration as a function of the depth of drilling; a sixth series of values that expresses the trend of the concentration of said at least one gas species belonging to the group of alkenes as a function of said depth of drilling and a seventh series of values that expresses the trend of the torque as a function of the drilling depth.

The system that allows implementation of the third embodiment of the present invention, in addition to the means described above, relatively to the first embodiment, comprises:
  means for measuring the torque at the drill bit;
  means for storing the measurements of torque at the drill bit;
  means for the processing of said measurements of torque at the drill bit;
  means for the extraction and the collection of the cuttings from the drilling mud;
  means for the analysis of the microscopic structure of said cuttings comprising, in turn, a high-resolution optical microscope.

The method and relative system described above achieve the proposed aims, overcoming the disadvantages noted in the prior art.

Thanks to the measurement of the concentration of the alkene gases and to the integration of these measurements with the measurement of the rate of penetration of the auger, it is possible, in fact, to be able to identify very early any malfunctionings of the drill bit, and to avoid considerable waste of hours of work that would occur if drilling continued with a damaged drill bit or not suitable for the type of well being worked. Finally, thanks to the integration of the measurements mentioned above with the measurement of the torque at the drill bit and with the observation of the variations in the microscopic structure of the drilling cuttings, a further confirmation is obtained of the supposed malfunctionings of the drill bit, thus obtaining an even more reliable method for early detection of these malfunctionings.

What is claimed is:

1. A method for the identification of malfunctioning of the drill bit during the drilling of hydrocarbon wells with the following steps:
    measurement of the drilling depth, obtaining a first time series of the values assumed by said drilling depth, said first time series being stored in a computer;
    measurement of the rate of penetration of the auger during drilling, obtaining a second time series of the values assumed by said rate of penetration, said second time series being stored in a computer;
    extraction of the drilling mud;
    degassing of said drilling mud;
wherein the method further comprises the following steps:
    measurement of the concentration in the drilling mud of at least one gas species belonging to the group of the alkenes, obtaining of at least one third time series of the values assumed of said concentration of said at least one gas species, said at least third time series being stored in a computer;
    for each sample of said second time series, comparison of the value of the rate of penetration corresponding to said sample, with a first threshold value, said step of comparison being carried out by the processor of a computer;
    if the value of said rate of penetration, at a time sample, is below said first threshold value, performing of the following operations:
        calculation of a mean value of said rate of penetration, over a time interval, said interval beginning at said time sample and said interval and comprising a sufficient number of time samples for covering an interval of drilling length greater than or equal to a second threshold value, said operation of calculating the mean value being performed by a processor of a computer;
        comparison of said mean value with said first threshold value, said operation of comparison being performed by a processor of a computer;
        for each sample of said third time series comprised in said time interval, comparison of the value of concentration of said at least one gas species with a third threshold value, said operation of comparison being performed by a processor of a computer.

2. The method according to claim 1, wherein said method comprises:
    generation, by means of a processor, of an alert signal, said signal being indicative of the fact that the auger has to be returned to the surface and the drill bit replaced, if said mean value is below said first threshold value, and if the value of the concentration of said at least one gas species in at least one time sample comprised in said time interval is greater than said third threshold value.

3. The method according to claim 2, wherein said method comprises:
    taking of a sample of cuttings contained in said drilling mud;
    analysis of said sample of cuttings by means of the display of their microscopic structure, said display being aimed at seeking possible vitrifications and carbonisations of the sample.

4. The method according to claim 1, wherein the following step is provided:
    measurement of the torque of the drill bit, obtaining a fourth time series of the values assumed by said torque, said fourth time series being stored in a computer;
    generation, by means of said processor, of a second alert signal, said second signal being indicative of the fact that the auger has to be returned to the surface and the drill bit replaced; if said mean value is below said first threshold value, the value of the concentration of said at least one gas species in at least one time sample comprised in said interval of time samples is greater than said third threshold value; and if said fourth time series assumes an erratic trend.

5. The method according to claim 4, wherein said erratic trend is identified by means of mathematical tests apt to determine the non-predictability of the values assumed by said fourth time series.

6. The method according to claim 5, wherein said method comprises:
    taking of a sample of cuttings contained in said drilling mud;
    analysis of said sample of cuttings by means of the display of their microscopic structure, said display being aimed at seeking possible vitrifications and carbonisations of the sample.

7. The method according to claim 4, wherein said method comprises:
    taking of a sample of cuttings contained in said drilling mud;
    analysis of said sample of cuttings by means of the display of their microscopic structure, said display being aimed at seeking possible vitrifications and carbonisations of the sample.

8. The method according to claim 1, wherein said method comprises:
    taking of a sample of cuttings contained in said drilling mud;
    analysis of said sample of cuttings by means of the display of their microscopic structure, said display being aimed at seeking possible vitrifications and carbonisations of the sample.

9. The method according to claim 8, wherein the sample of cuttings is taken at intervals corresponding to a drilling length greater than or equal to 2 m.

10. The method according to claim 9, wherein said sample of cuttings weighs between 50 and 100 g.

11. The method according to claim 1, wherein said first threshold value is 2 m/h.

12. The method according to claim 1, wherein said second threshold value is 5 m.

13. The method according to claim 1, wherein said third threshold value is 25 ppm.

14. The method according to claim 1, wherein said at least one gas species belonging to the group of alkenes is ethylene or propylene.

15. The method according to claim 1, wherein at least one of the following steps is provided:
    creation of a series of values of the rate of penetration as a function of the drilling depth, by means of an operation of average of the values of the rate of penetration over a time interval, equal to that necessary for covering a unit of length of the drilling depth;
    creation of at least one series of values of the concentration of said at least one gas species belong to the group of the alkenes as a function of the drilling depth, by means of an operation of average of the values of the concentration of said at least one gas species, over a time interval, equal to that necessary for covering a unit of length of the drilling depth.

16. A system for the identification of malfunctioning of the drill bit during the drilling of hydrocarbon wells by means of the method according to claim 1, wherein said system comprises:

means for measuring the rate of penetration of the auger;

means for measuring the drilling length;

means of extraction of the drilling mud of at least one gas species belonging to the group of the alkenes comprising a filtration probe and a degasser;

means for measuring the concentration of said at least one gas species in the drilling mud, comprising a flame ionisation detector;

means for the storage of the measurements of the drilling speed, of drilling length and of concentration of said at least one gas species;

means for the processing of the measurements of rate of penetration, of the drilling length and of said at least one gas species;

means for the generation of an alert signal, on the basis of the results of said processing, said alert signal being indicative of the need to bring back to the surface the auger and replace the drill bit.

17. The system for the identification of malfunctioning of the drill bit according to claim 16, said system comprising: means for measuring the torque at the drill bit.

18. The system of claim 17, wherein the means for measuring the torque at the drill bit comprises hydraulic sensors.

19. The system according to claim 16, said system comprising means for the analysis of the microscopic structure of drilling cuttings.

20. The system of claim 19, wherein the means for the analysis of the microscopic structure of the drilling cuttings comprises an optical microscope with high resolution.

* * * * *